United States Patent [19]

Nakazawa et al.

[11] Patent Number: 4,571,285

[45] Date of Patent: Feb. 18, 1986

[54] OXYGEN SENSOR FOR AND METHOD OF DETERMINING CONCENTRATION OF OXYGEN

[75] Inventors: Mitsuhiro Nakazawa, Sakura; Hiroshi Osanai, Tokyo; Yoshiya Isono, Funabashi; Akiyoshi Asada, Tokyo; Hitoshi Ohira, Sakura, all of Japan

[73] Assignee: Fujikura Ltd., Tokyo, Japan

[21] Appl. No.: 738,150

[22] Filed: May 24, 1985

[30] Foreign Application Priority Data

May 29, 1984 [JP] Japan .................. 59-108945
Jul. 25, 1984 [JP] Japan .................. 59-153038

[51] Int. Cl.[4] ............................ G01N 27/56
[52] U.S. Cl. ........................... 204/1 T; 204/425
[58] Field of Search ............... 204/424, 425, 1 S

[56] References Cited

U.S. PATENT DOCUMENTS 4,310,402  1/1982  Isenberg et al. ............. 204/424 X
4,381,224  4/1983  Fate et al. .................. 204/425 X Primary Examiner—G. L. Kaplan
Attorney, Agent, or Firm—Sprung Horn Kramer & Woods

[57] ABSTRACT

An oxygen sensor for determining the partial pressure of oxygen in a monitored gas environment includes a diffusion housing of zirconia based material having a gas diffusion aperture, an oxygen ion conductive plate of zirconia based material, a pair of electrode layers mounted on opposite sides of the conductive plate, and a sealing glass material sealingly bonding the conductive plate at one side to the housing to provide a diffusion chamber defined by the diffusion housing and the conductive plate. The electrodes are connectable to a power source for being supplied with an electric potential to pump oxygen ion out of the diffusion chamber through the conductive plate to flow a current through the electrodes which current is indicative of the partial pressure of the oxygen in the monitored gas environment. The sealing glass material contains $SiO_2$, $BaO$, $Na_2O$ and $ZrO_2$.

6 Claims, 9 Drawing Figures

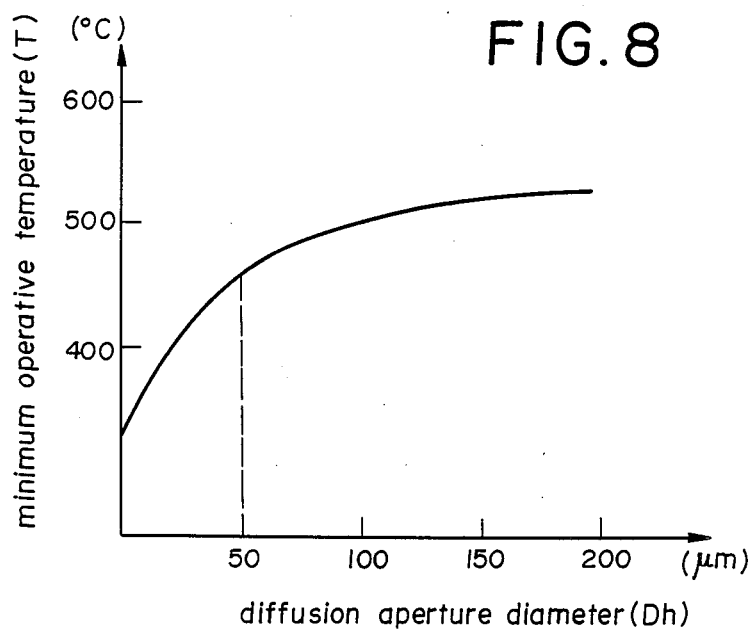
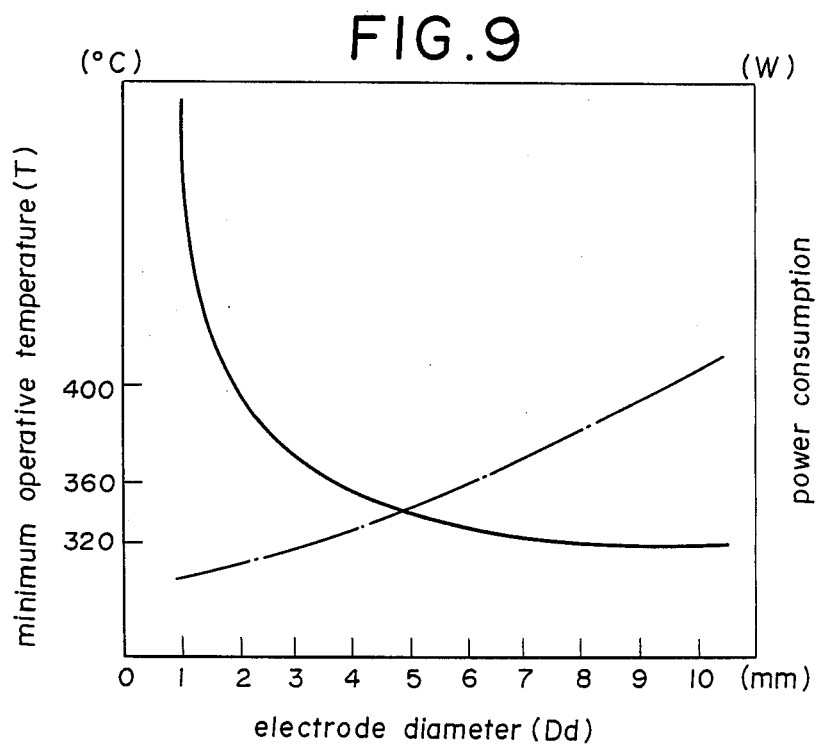

OXYGEN SENSOR FOR AND METHOD OF DETERMINING CONCENTRATION OF OXYGEN

BACKGROUND OF THE INVENTION

1. Field of the Invention

This invention relates to an oxygen sensor for and a method of determining the concentration of oxygen (i.e., the partial pressure of oxygen) in a monitored gas environment.

2. Prior Art

One conventional oxygen sensor 10 shown in FIG. 1 comprises a diffusion housing 12, an oxygen ion conductive plate 14 of solid electrolyte hermetically bonded at one surface to the diffusion housing 12 by sealing glass 16, and a pair of circular electrode layers 18 and 18 secured to the opposite sides of the conductive plate 14, respectively, the electrodes 18 and 18 being connected to a DC power source 20. For example, the oxygen ion conductive plate 14 comprises a solid solution containing $ZrO_2$, $Y_2O_3$, MgO and CaO. Each of electrode layers 18 is porous and is made, for example, of platinum. The diffusion housing 12 has a gas diffusion aperture 12a of a small diameter formed through a wall 12b. The diffusion of oxygen from the monitored gas environment G through the gas diffusion aperture 12a into a chamber 12c of the diffusion housing 12 is effected by the application of a DC potential from the power source 20 across the two electrodes 18 and 18 to pump oxygen present in the chamber 12c through the oxygen ion conductive plate 14. As the potential across the two electrodes 18 is increased, electrical current flowing through the two electrodes 18 is changed as indicated by a curve A in FIG. 2. The curve A is divided into three regions X, Y and Z. The region X is a transition region at which the above-mentioned pumping of the oxygen out of the chamber 12c is in the process of reaching a constant rate. At the region Y, the amount of the molecules of the oxygen flowing into the chamber 12c through the gas diffusion aperture 12a is equal to the amount of the molecules of the oxygen flowing out of the chamber 12c through the oxygen ion conductive plate 14. At this region, the current limited by the oxygen diffusion is rendered stable so that a stable diffusion limited current value Ip is obtained. At the region Z, the current flowing through the two electrodes 18 is abruptly increased because the current contains components other than the ion current, such as current caused by the electronic conduction. The diffusion limited current value Ip is proportional to the concentration of oxygen in the monitored gas environment G, and therefore the oxygen concentration is detected by measuring the diffusion limited current value Ip through an ammeter A.

Another conventional oxygen sensor 10a shown in FIG. 3 differs from the oxygen sensor 10 of FIG. 1 in that a diffusion housing 12 made of an open-cell porous structure is used with the gas diffusion aperture 12a being omitted. With this construction, the oxygen diffuses into the housing chamber 12c through the porous housing 12, and the pumping of oxygen out of the chamber 12c is effected as described above for the oxygen sensor of FIG. 1.

The sealing glass 16 sealingly bonding the oxygen ion conductive plate 14 to the diffusion housing 12 comprises amorphous glass containing $SiO_2$, BaO and $Na_2O$. The bond between the oxygen ion conductive plate 14 and the diffusion housing 12 must be maintained heat-resistant, airtight and thermal shock-resistant. The oxygen ion conductive plate 14 is made of zirconia, and the diffusion housing 12 is usually made of zirconia-based material so that there will not be provided a substantial difference in thermal expansion coefficient between the conductive plate 14 and the diffusion housing 12. Therefore, the diffusion housing 12 and the oxygen ion conductive plate 14 have a relatively high thermal expansion coefficient, for example, of $100 \times 10^{-7}/°$ C., and must have such a thermal resistance as to withstand up to 800° C. For these reasons, the bond between the diffusion housing 12 and the oxygen ion conductive plate 14 must be made through glass. However, it is rather difficult to manufacture such glass as to meet these requirements. Glass containing $SiO_2$, BaO and $Na_2O$ is the only glass which is commercially available, partially amorphous and somewhat analoguous in physical properties to the above-mentioned desired glass. This amorphous glass has a poor thermal shock resistance, and a crack is liable to develop in it.

SUMMARY OF THE INVENTION

It is therefore an object of this invention to provide an oxygen sensor of the type in which the diffusion housing and the oxygen ion conductive plate are sealingly bonded together by amorphous glass having a high thermal expansion coefficient and excellent thermal resistance and thermal shock resistance.

According to the present invention, there is provided an oxygen sensor for determining the partial pressure of oxygen in a monitored gas environment which comprises a diffusion housing of zirconia based material having a gas diffusion aperture, an oxygen ion conductive plate of zirconia based material, a pair of electrode layers mounted on opposite sides of the conductive plate, and a sealing glass material sealingly bonding the conductive plate at one side to the housing to provide a diffusion chamber defined by the diffusion housing and the conductive plate, the electrodes being connectable to a power source for being supplied with an electric potential to pump oxygen ion out of the diffusion chamber through the conductive plate to flow a current through the electrodes which current is indicative of the partial pressure of the oxygen in the monitored gas environment, and the sealing glass material containing $SiO_2$, BaO, $Na_2O$ and $ZrO_2$.

BRIEF DESCRIPTION OF THE DRAWINGS

FIG. 8 is a diagrammatical illustration between the minimum operative temperature and the diameter of the gas diffusion aperture; and FIG. 9 is a diagrammatical illustration showing the relation between the minimum operative temperature and the electrode diameter as well as the relation between the power consumption and the electrode diameter.

DESCRIPTION OF THE PREFERRED EMBODIMENT OF THE INVENTION

Figure 1:
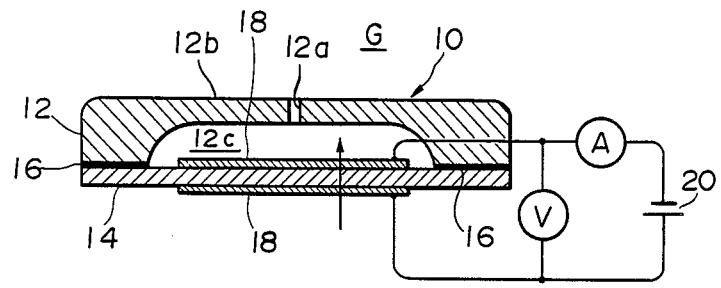
FIG. 1 is a cross-sectional view of an oxygen sensor provided in accordance with the prior art.
Figure 2:
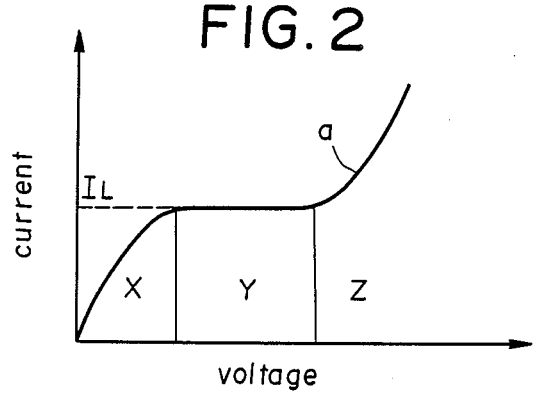
FIG. 2 is a diagrammatical illustration showing a change in current flowing through electrodes of the oxygen sensor.
Figure 3:
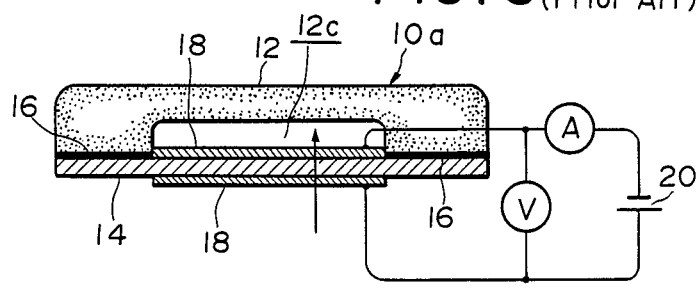
FIG. 3 is a view similar to FIG. 1 but showing another conventional oxygen sensor.
Figure 4:
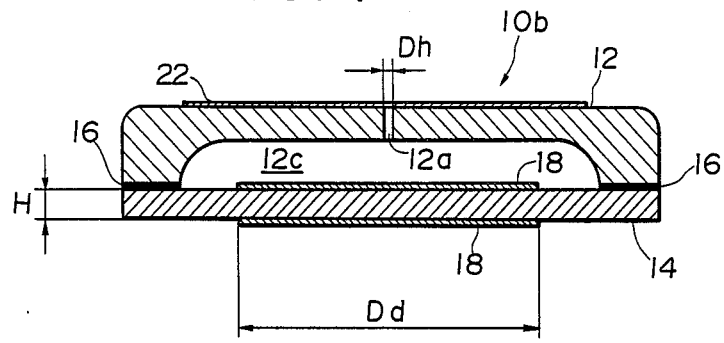
FIG. 4 is a view similar to FIG. 1 but showing an oxygen sensor provided in accordance with the present invention.

An oxygen sensor 10b shown in FIG. 4 is identical in construction to the oxygen sensor 10 of FIG. 1, and corresponding parts are designated by like reference numerals. The oxygen sensor 10b comprises electric heating means 22 for heating the oxygen sensor to a predetermined temperature during an operation thereof, the heating means 22 being in the form of a pattern of a continuous resistance heating element formed on the outer surface of the housing 12 facing away from the oxygen ion conductive plate 14. The heating means 22 is connected to a power source (not shown) for being energized.

A sealing material 16 which sealingly bonds an oxygen ion conductive plate 14 to a diffusion housing 12 is made of glass containing $SiO_2$, BaO, $Na_2O$ and $ZrO_2$. The sealing glass 16 is prepared by adding zirconia powder to amorphous glass containing $SiO_2$, BaO and $Na_2O$, the amorphous glass having an operating temperature of about 1000° C. and having a relatively high thermal expansion coefficient of $90 \times 10^{-7}/°$ C. which is relatively close to that of zirconia. A typical example of such amorphous glass commercially available is one sold by Iwaki Glass Co., Ltd. (Japan) under the tradename of #9010 of which composition is represented in Table 1 in terms of both elements and oxides:

TABLE 1

| Si: | 33.0% | $SiO_2$: | 70.6% |
|---|---|---|---|
| Ba: | 9.6% | BaO: | 10.7% |
| Na: | 5.4% | $Na_2O$: | 7.3% |
| K: | 4.7% | $K_2O$: | 5.7% |
| Al: | 1.5% | $Al_2O_3$: | 2.8% |
| Li: | 0.7% | $Li_2O$: | 1.5% |
| | | Total: | 98.6% |

The above amorphous glass has the following characteristics:

TABLE 2

| Thermal expansion coefficient ($10^{-7}$/in/°C. (50 to 100° C.) | | 96 |
|---|---|---|
| Operating temperature (°C.) | | 1000 |
| Softening point (°C.) | | 665 |
| Annealing point (°C.) | | 445 |
| Distortion point (°C.) | | 410 |
| Density (gr/cc) | | 2.60 |
| Volume resistance ($\log_{10} \rho$) | 25° C. | 17 |
| ($\Omega-cm$) | 150° C. | 12 |
| | 350° C. | 7 |
| Dielectric constant | 1 MC | 7 |
| | 3 MC | 7 |
| $\tan \delta \times 10^4$ | 1 MC | 20 |
| | 3 MC | 50 |

The amount of addition of zirconia to such amorphous glass to form the sealing glass material 16 should be 1 to 30% of the total weight of the glass and the zirconia. If the zirconia content is less than 1%, desired results can not be achieved. On the other hand, if this content exceeds 30%, the vitrification of the mixture of the amorphous glass and zirconia is adversely affected. Preferably, the zirconia powder to be added to the amorphous glass should have a particle size of not more than 3 μm.

The zirconia powder added to the amorphous glass containing $SiO_2$, BaO and $Na_2O$ is dispersed therein to serve as cushioning means for absorbing shock applied to the resultant sealing glass material. Thus, the zirconia powder so added serves to reinforce the sealing glass material.

The invention will now be illustrated by way of the following Example:

EXAMPLE 1

10% by weight of zirconia powder was added to amorphous glass shown in Tables 1 and 2 to form a sample glass material A of this invention. According to the same procedure, a sample glass material B of this invention having a zirconia content of 15% and a sample glass material C of this invention having a zirconia content of 20% were prepared. The above amorphous glass with no zirconia content was used as a comparative sealing glass material D.

Each of the sealing glass materials A, B, C and D was used to provide an oxygen sensor similar to that shown in FIG. 4. The diffusion housing was made of zirconia solid solution partially stabilized by 3 mol. % of $Y_2O_3$ having a thermal expansion coefficient of $92 \times 10^{-7}/°$ C. The oxygen ion conductive plate was made of solid electrolyte of zirconia stabilized into a generally cubic crystal structure by 8 mol. % of $Y_2O_3$ having a thermal expansion coefficient of $100 \times 10^{-7}/°$ C.

10 samples were tested with respect to each of the sealing glass materials A to D to determine how many samples out of ten were subjected to a crack both at the time when the sealing glass material was initially heated from room temperatures to 400° C. and at the time when the sealing glass was subjected to 100 cycles of heat shock from 400° C. to room temperatures. The results obtained are shown in Table 3 below.

TABLE 3

| Sample | Initial temp. rise (room temp. to 400° C.) | 100 heat shock cycles (400° C. ⟷ room temp.) |
|---|---|---|
| A | 0/10 | 0/10 |
| B | 0/10 | 0/10 |
| C | 0/10 | 0/10 |
| D | 3/10 | 7/10 |

As can be seen from Table 3, none of the sample glass materials A, B and C were subjected to a crack both at the initial temperature rise from room temperatures to 400° C. and during 100 cycles of heat shock from 400° C. to room temperatures. On the other hand, three out of ten comparative sample glass material D were subjected to a crack at the initial temperature rise, and seven out of ten comparative glass material D underwent a crack during 100 cycles of heat shock.

One example of the amorphous glass containing $SiO_2$, BaO and $Na_2O$ has been shown in Table 1, but the content of each component of this glass can be varied in the range of ±5%.

$SiO_2$ is a major component of the amorphous glass and cooperates with BaO to promote the solidification rate. $Na_2O$ renders the glass soft so that the glass can be processed easily, but it has a relatively high thermal expansion coefficient. However, the addition of K₂O lowers the thermal expansion coefficient. Al₂O₃ also lowers a thermal expansion coefficient and increases a weathering resistance and a resistance to acids and alkalis. LiO₂ tends to enhance crystallinity and therefore improves a heat resistance.

According to the present invention, zirconia ($ZrO_2$) is added to the above amorphous glass to provide the sealing glass material. The diffusion housing and the oxygen ion conductive plate which are bonded together through the sealing glass material are both made of zirconia-based material, and therefore the sealing glass material provides for higher bonding ability and heat resistance.

Referring again to FIG. 4, the oxygen ion conductive plate 14 has a thickness H of 0.08 to 0.8 mm. Each of the electrodes 18 has a diameter Dd of not more than 7 mm. The gas diffusion aperture 12a has a diameter Dh of 10 to 50 μm. The oxygen sensor 10b is maintained at temperatures of about 350° to 450° C. by the heating means 22 during the operation thereof.

Figure 5:
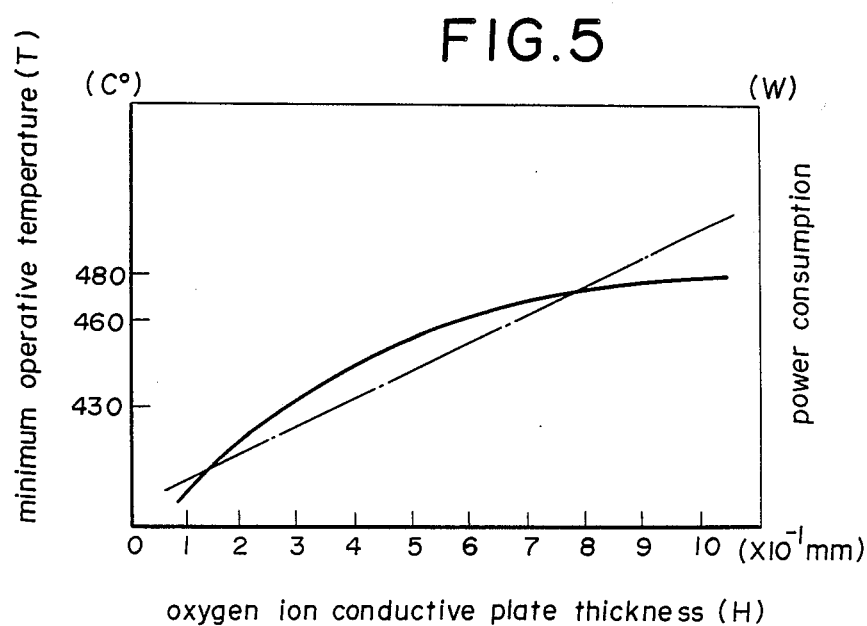
FIG. 5 is a diagrammatical illustration showing the relation between an oxygen ion conductive plate and the minimum operative temperature as well as the relation between the conductive plate and the power consumption.

The thickness H of the oxygen ion conductive plate 14 is linearly increased with the increase of power consumption W as indicated in a dash-and-dot line in FIG. 5, but the minimum operative temperature T becomes generally constant when the thickness H exceeds 0.8 mm as indicated in a solid line in FIG. 5. The minimum operative temperature T means the lower limit of the temperature range in which the diffusion limited current can be probed in the atmosphere (in which the oxygen concentration is almost constant). Therefore, in view of heating efficiency, the thickness H should not be more than 0.8 mm. More preferably, the thickness H should be about 0.5 mm in view of the strength and fabrication of the oxygen ion conductive plate 14. The thickness H should not be less than 0.08 mm. The oxygen ion conductive plate 14 is made of sintered ceramics, and if the thickness H is below 0.08 mm, the plate 14 is rendered impractical because of the presence of the voids or pores between the particles of the sintered ceramics.

When the oxygen sensor 10b operates at temperatures of around 500° C., the electrodes 18 of platinum and the oxygen ion conductive plate 14 of solid electrolyte are much deteriorated, so that the oxygen sensor 10b can not be used for a long period of time. It has now been found that such deterioration will not occur when the oxygen sensor 10b operates at temperatures of not more than 450° C. Also, it has been found that the minimum operating temperature of the oxygen sensor 10b is 300° C. If the operating temperature is less than 300° C., the oxygen ion conductive ability is lowered to such an extent that the oxygen sensor 10b does not function properly.

Figure 6:
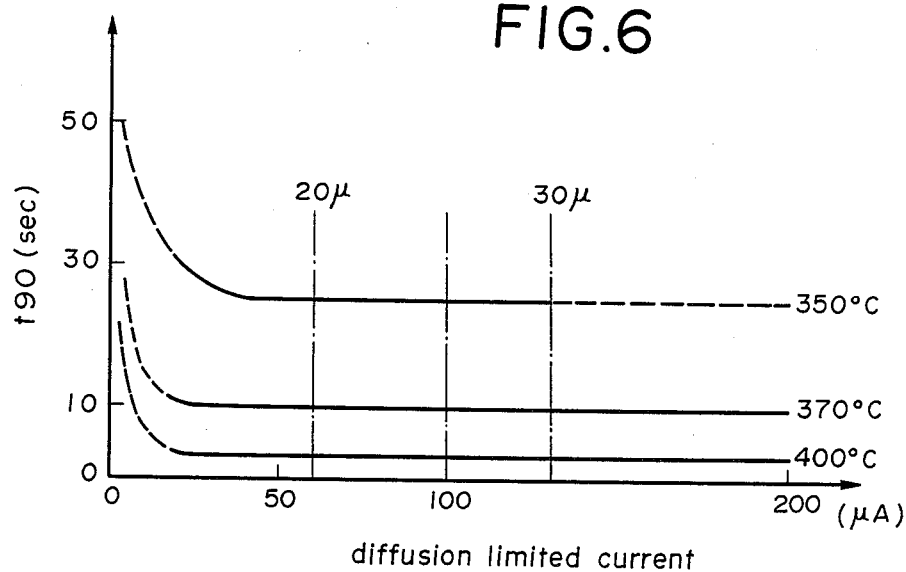
FIG. 6 is a diagrammatical illustration between the response time and the diffusion limited current.
Figure 7:
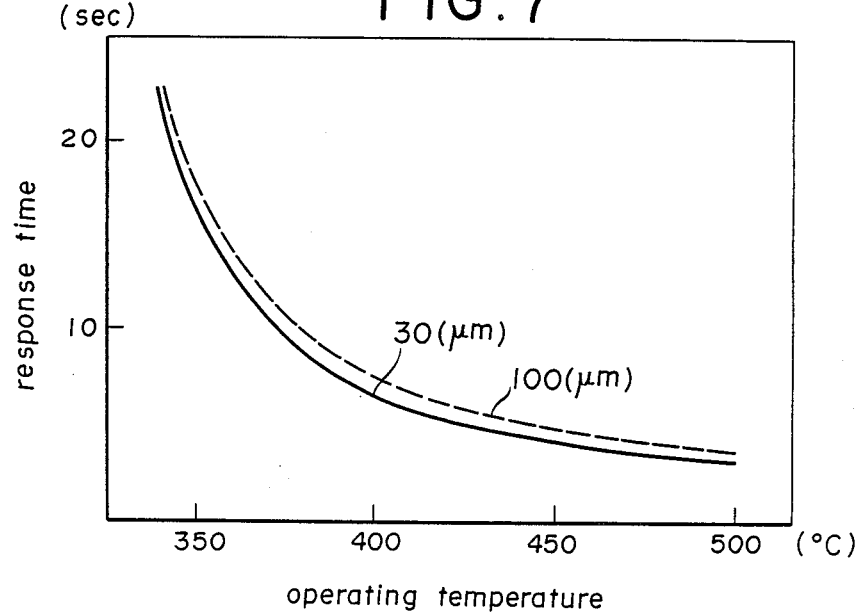
FIG. 7 is a diagrammatical illustration between the response time and the operating temperature of the oxygen sensor.

More specifically, the practical operating temperature of the oxygen sensor 10b is seen from FIGS. 6 and 7. The oxygen sensor 10b must be heated to the above minimum operating temperature in order to achieve a satisfactory response. The satisfactory response is achieved when the change of oxygen concentration by 90% is indicated within 10 seconds.

FIGS. 6 and 7 show the relation between the response and operating temperature of the oxygen sensor 10b.

FIG. 6 shows the relation between response time $t_{90}$ (i.e., the time required before the oxygen sensor indicates the occurrence of the change of oxygen concentration by 90%.) and the value of diffusion limited current. The depth or length of the gas diffusion aperture 12a is predetermined, that is to say, 1 mm, and therefore the value of the diffusion limited current is determined in accordance with the diameter Dh of the gas diffusion aperture 12a. The response time is determined solely in accordance with the operating temperature of the oxygen sensor 12a when the diameter Dh of the gas diffusion aperture 12a is more than a predetermined value which is about 10 μm. Therefore, it is necessary that the operating temperature should not be less than 370° C. to achieve the satisfactory practical response.

FIG. 7 also shows the relation between the response time and the operating temperature (i.e., the temperature of the oxygen sensor 10b). In FIG. 7, a broken line indicates the relation when the diameter Dh of the gas diffusion aperture 12a is 100 μm, and a solid line indicates the relation when the diameter Dh is 30 μm. As can be seen from FIG. 7, the response time will not be changed substantially even if the value of the diameter Dh is varied substantially. This indicates that the essential factor in determining the response time is not the diameter Dh of the gas diffusion aperture 12a which corresponds to a diffusion resistance but the operating temperature of the oxygen sensor 10b. As can be seen from FIG. 7, in order to achieve the satisfactory practical response, the operating temperature should be more than about 370° C. as is the case with the relation shown in FIG. 6. Actually, it has been found that the operating temperature of not less than 350° C. can achieve substantially the same response.

FIG. 8 shows the relation between the minimum operative temperature and the diameter Dh of the gas diffusion aperture 12a, with the length of the aperture 12a being 1 mm. The upper limit of the operating temperature is 450° C. as described above. In order that 450° C. may be the minimum operative temperature, the diameter Dh is not more than about 50 μm. With respect to the lower limit of the operating temperature, the diameter Dh is about 10 μm as described above for the response. Therefore, the diameter Dh should be about 10 to about 50 μm.

FIG. 9 shows the relation between the minimum operative temperature and the diameter Dd of each electrode 18 (solid line), the power consumption being indicated in a dash-and-dot line. As the electrode diameter Dd increases, the power consumption required increases. However, when the electrode diameter Dd exceeds about 7 mm, the minimum operative temperature becomes generally constant and will not be further lowered. Therefore, the electrode diameter Dd should not be more than about 7 mm.

What is claimed is:

1. An oxygen sensor for determining the partial pressure of oxygen in a monitored gas environment which comprises a diffusion housing of zirconia based material having a gas diffusion aperture, an oxygen ion conductive plate of zirconia based material, a pair of electrode layers mounted on opposite sides of said conductive plate, and a sealing glass material sealingly bonding said conductive plate at one side to said housing to provide a diffusion chamber defined by said diffusion housing and said conductive plate, said electrodes being connectable to a power source for being supplied with an electric potential to pump oxygen ion out of said diffusion chamber through said conductive plate to flow a current through said electrodes which current is indicative of the partial pressure of the oxygen in the monitored gas environment, and said sealing glass material containing $SiO_2$, $BaO$, $Na_2O$ and $ZrO_2$.

2. An oxygen sensor according to claim 1, in which said sealing glass material is prepared by the steps of providing amorphous glass containing $SiO_2$, $BaO$ and $Na_2O$ and adding zirconia powder to said amorphous glass.

3. An oxygen sensor according to claim 2, in which said amorphous glass contains 70.6% by weight of $SiO_2$, 10.7% of $BaO$, 7.3% of $Na_2O$, 5.7% of $K_2O$, 2.8% of $Al_2O_3$ and 1.5% of $Li_2O$.

4. An oxygen sensor according to claim 2, in which said zirconia powder has a particle size of not more than 3 μm.

5. An oxygen sensor according to claim 1 or claim 2, in which the zirconia content of said sealing glass material is 1 to 30% by weight.

6. A method of determining the partial pressure of oxygen in a monitored gas environment which comprises the steps of:
(a) providing an oxygen sensor which comprises a diffusion housing of zirconia based material having a gas diffusion aperture, an oxygen ion conductive plate of zirconia based material, a pair of electrode layers mounted on opposite sides of said conductive plate, heating means mounted on said housing, and a sealing glass material sealingly bonding said conductive plate at one side to said housing to provide a diffusion chamber defined by said diffusion housing and said conductive plate, said electrodes being connectable to a power source for being supplied with an electric potential to pump oxygen ion out of said diffusion chamber through said conductive plate to flow a current through said electrodes which current is indicative of the partial pressure of the oxygen in the monitored gas environment, said sealing glass material containing $SiO_2$, $BaO$, $Na_2O$ and $ZrO_2$, each of said oxygen ion conductive plate having a thickness of 0.08 to 0.8 mm, each of said electrode layers having a circular shape and a diameter of not more than 7 mm, and said gas diffusion aperture having a length of 1 mm and a diameter of 10 to 50 μm; and
(b) operating said heating means to maintain said oxygen sensor at temperatures of about 350° C. to about 450° C. and operating said oxygen sensor to determine the partial pressure of the oxygen in the monitored gas environment.

* * * * *